United States Patent
Orita et al.

(10) Patent No.: US 7,279,596 B2
(45) Date of Patent: Oct. 9, 2007

(54) STABLE CRYSTALS OF SUBSTITUTED PHENYLPROPIONIC ACID DERIVATIVE AND PROCESS FOR PRODUCING THE SAME

(75) Inventors: Kazuo Orita, Hasuda (JP); Tomomi Koike, Nogi-machi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 342 days.

(21) Appl. No.: 10/497,174

(22) PCT Filed: Dec. 10, 2002

(86) PCT No.: PCT/JP02/12892

§ 371 (c)(1),
(2), (4) Date: May 5, 2005

(87) PCT Pub. No.: WO03/050077

PCT Pub. Date: Jun. 19, 2003

(65) Prior Publication Data

US 2005/0228050 A1   Oct. 13, 2005

(30) Foreign Application Priority Data

Dec. 11, 2001 (JP) .............................. 2001-377077

(51) Int. Cl.
*C07C 63/00* (2006.01)
*A61K 31/195* (2006.01)

(52) U.S. Cl. ..................................... 562/405; 514/562

(58) Field of Classification Search ..................... None
See application file for complete search history.

(56) References Cited

U.S. PATENT DOCUMENTS 6,506,797 B1 *   1/2003   Nomura et al. ............. 514/562

FOREIGN PATENT DOCUMENTS

| CA | 2 376 094 A1 | 12/2000 |
| WO | 00/75103 | 12/2000 |
| WO | 01/21578 | 3/2001 |
| WO | 01/25181 | 4/2001 |

OTHER PUBLICATIONS

Laszlo Borka, et al., "Crystal polymorphism of pharmaceuticals", Acta Pharm. Jugosl., vol. 40, XP-009031944, 1990, pp. 71-94.

* cited by examiner

*Primary Examiner*—Samuel Barts
(74) *Attorney, Agent, or Firm*—Oblon, Spivak, McClelland, Maier & Neustadt, P.C.

(57) ABSTRACT

Preparation of (S)-2-[[3-[N-[4-[(4-fluorophenoxy)phenyl]methyl]carbamoyl]-4-methoxyphenyl]methyl]butanoic acid (referred to as compound (I)) on an industrial scale lies in the finding of crystals homogeneous and excellent in the stability and the establishment of a preparative process thereof.

Novel crystals of compound (I) homogeneous and excellent in the stability characterized by exhibiting the diffraction angles (2θ) at at least 17.7°, 19.0° and 24.1° in the X-ray powder diffraction are provided by recrystallizing from an alcoholic solvent and purifying by acid-base treatment.

4 Claims, 4 Drawing Sheets

STABLE CRYSTALS OF SUBSTITUTED PHENYLPROPIONIC ACID DERIVATIVE AND PROCESS FOR PRODUCING THE SAME

TECHNICAL FIELD

The present invention relates to a stable crystal form of (S)-2-[[3-[N-[4-[(4-fluorophenoxy)phenyl]methyl]-carbamoyl]-4-methoxyphenyl]methyl]butanoic acid (hereinafter referred to as compound (I)) represented by a formula (I)

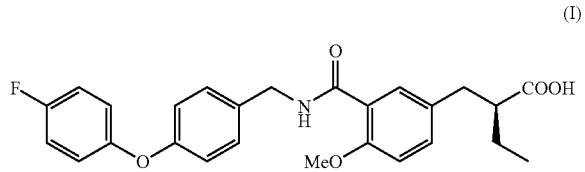

and process for the preparation thereof.

BACKGROUND TECHNOLOGY

Compound (I) is a useful compound for the therapy of the abnormality of lipid metabolism as an agonist of human peroxisome proliferator-activated receptor (PPAR), in particular, as an agonist of human PPARα isoform, and has been prepared through a process disclosed in Jpn. Kokai Tokkyo Koho JP 2001-55367.

Preparation of the compound (I) on an industrial scale as a medicinal drug lies in the finding of crystals homogeneous and excellent in the stability and yet the establishment of a preparative process thereof.

DISCLOSURE OF THE INVENTION

When having advanced the research and development on the physical properties and preparative process of compound (I), the inventors have found that new type crystals more stable and richer in the homogeneity being different from the crystals (referred to as old type crystals) obtainable through the conventional process (Jpn. Kokai Tokkyo Koho JP 2001-55367) can be obtained on an industrial scale, leading to the completion of the invention. Namely, it has been ascertained that, if recrystallizing the crude crystals of compound (I) prepared according to the conventional process from a suitable solvent, then stable and homogeneous crystals (referred to as new type crystals) that exhibit higher melting point than that of old type crystals can be obtained. Furthermore, it has become clear that, if purifying these new type crystals by acid-base treatment, new type crystals in the state of containing no residual solvent in the crystals can be taken out. Moreover, it has also been identified that, by further recrystallizing the old type crystals obtained through the conventional process with a suitable solvent as described above, it is possible to convert them into the inventive new type crystals. In this way, the new type crystals of compound (I) with more preferable properties as original powder of medicinal drug and the preparative process have been found, leading to the completion of the invention.

The new type crystals of compound (I) are crystals characterized by exhibiting the diffraction angles (2θ) at at least 17.7°, 19.0° and 24.1° in the X-ray powder diffraction. Moreover, they have higher melting point than that of conventional crystals.

The new type crystals of compound (I) can usually be obtained in good reproducibility, if recrystallizing the crude crystals obtained after completion of the reaction from a suitable solvent and successively purifying by acid-base treatment.

As the solvents to be used for recrystallization, lower alcohols such as ethanol and water-containing lower alcohols can be mentioned. Preferable solvent is water-containing ethanol or water-containing isopropyl alcohol, and it may also be safe to dissolve previously into alcohol and then add water. The acid-base treatment is performed by dissolving the new type crystals obtained by recrystallization into a common inorganic base, preferably aqueous solution of sodium hydroxide or potassium hydroxide, neutralizing with a common acid, preferably hydrochloric acid under warming, preferably at 50° C. or so, and filtering and washing the precipitated crystals.

The new type crystals obtainable according to the invention have no hygroscopicity, make stable supply possible in terms of preparation, and leave no residual organic solvent. Such new type crystals are very advantageous for the industrial production of compound (I).

Best Embodiment to Put the Invention into Practice

In following, the invention will be illustrated in more detail showing examples, but the invention is not confined to these examples at any rate.

EXAMPLE 1

Preparation of New Type Crystals of (S)-2-[[3-[N-[4-[(4-fluorophenoxy)phenyl]methyl]carbamoyl]-4-methoxyphenyl]methyl]butanoic acid (compound (I))

To a solution of 104 g (0.207 mol) of benzyl 5-[3-[4-(R)-benzyl-2-oxo-1,3-oxazolidine-3-yl]-2-(S)-ethyl-3-oxopropyl]-2-methoxybenzoate (Jpn. Kokai Tokkyo Koho JP 2001-55367 (Example 165)) in 728 ml of ethyl acetate (AcOEt) were added 6.93 g of 10% palladium on carbon (Pd—C) (dry article), and the mixture was stirred for 5 hours at inner temperature of 35° C. under an atmosphere of hydrogen. After the catalyst was filtered off, the reaction mixture was concentrated under reduced pressure to obtain colorless oily 5-[3-[4-(R)-benzyl-2-oxo-1,3-oxazolidine-3-yl]-2-(S)-ethyl-3-oxopropyl]-2-methoxybenzoic acid. This oily product was dissolved into 413 mL of dehydrated dimethylformamide (DMF) and, after 62.9 g (0.622 mol) of triethylamine (Et₃N) were added, the mixture was stirred under cooling with ice water. At inner temperature of 5° C., 22.5 g (0.207 mol) of ethyl chloroformate were added dropwise (inner temperature increased to 8° C.) and thereafter the mixture was stirred for 1 hour. Then, 55.2 g (0.218 mol) of [4-(4-fluorophenoxy)phenyl]methylamine hydrochloride were put in at inner temperature of 6° C. and the mixture was stirred for 1 hour. The reaction mixture was poured into 826 mL of water, which was extracted twice (516 mL, 309 mL) with ethyl acetate. The ethyl acetate layers were combined, washed with 207 mL of 1 mol/L aqueous solution of sodium hydroxide (NaOH aq.), 405 mL of water and 36 mL of saturated brine in sequence, then dried over anhydrous sodium sulfate, and solvent was distilled off under reduced pressure. The product was dried (vacuum pump) for 2 hours at room temperature under reduced pressure to obtain 126 g of pale yellow oily N-[4-(4-fluorophenoxy)phenyl]methyl-5-[3-[4-(R)-benzyl-2-oxo-1,3-oxazolidine-3-yl]-2-(S)-ethyl-3-oxopropyl]-2-methoxybenzamide. This oily product was dissolved into 806 mL of tetrahydrofuran (THF) and, after 202 mL of purified water were added, the mixture was stirred under cooling with ice water. To this solution were added dropwise 91 mL (0.829 mol) of 31% aqueous hydrogen peroxide ($H_2O_2$) over 10 minutes at inner temperature of 8° C. Following this, a solution of 13.9 g (0.332 mol) of lithium hydroxide monohydrate ($LiOH.H_2O$) in 556 mL of purified water were added dropwise over 80 minutes at inner temperature of 8 to 10° C. and the mixture was stirred further for 1 hour. After a solution of 86.2 g of sodium hydrogensulfite ($NaHSO_3$) in 432 mL of purified water were added dropwise over 20 minutes, the mixture was stirred for 1 hour. After allowed to stand statically, the aqueous layer was separated, which was extracted with 259 mL of ethyl acetate pH value of aqueous layer 1.33: pH meter). The organic layers were combined and solvent was distilled off under reduced pressure. The residue was dissolved into 518 mL of ethyl acetate and, after washing with 415 mL of cold water, the solution was extracted twice with cold aqueous solution of alkali prepared with 570 mL of ice water and 570 mL of 1 mol/L NaOH aq. The aqueous layers were combined and 273 mL of 6 mol/L hydrochloric acid (HCl aq.) were added, which was then extracted with 829 mL and 311 mL of ethyl acetate. The ethyl acetate layers were combined, washed with 270 mL of saturated aqueous solution of sodium hydrogencarbonate (pH value of washed liquid: 7.38, pH meter) and 41 mL of saturated brine in sequence, then dried over anhydrous sodium sulfate and concentrated under reduced pressure. To the residue were added 207 mL of ethyl acetate and 21 mL of isopropyl alcohol (IPA). After dissolved by heating, 311 mL of hexane were added. The mixture was stirred at room temperature under cooling by allowing to stand and stirred at inner temperature of 30° C. under cooling with ice water. After stirring for 1 hour at inner temperature of below 10° C., the precipitated crystals were collected by filtration at inner temperature of 6° C. After washing with 173 mL of mixed solution of hexane/ethyl acetate (3:1), the crystals were dried for 3 hours at 50° C. by blower to obtain 75.0 g of crude crystals of compound (I). After dissolved 75.0 g of crude crystals into 483 mL of ethanol (EtOH) by heating, 257 mL of purified water were added. After stirring under cooling with water, the solution was cooled with ice water at inner temperature of 25° C. and stirred for 1 hour at inner temperature of below 10° C. The precipitated crystals were collected by filtration at inner temperature of 4° C. and, after washing with 357 mL of 25% EtOH/water, the crystals were dried for 1 hour by blower. These were dried at 50° C. until they became constant weight to obtain 73.3 g (yield 78%) of the compound of the present application.

Furthermore, 73.3 g of these crystals were suspended into 344 mL of purified water and dissolved by adding 390 mL of 0.5 mol/L NaOH aq., followed by filtration. The filtrate was heated to inner temperature of 45 to 50° C. and, after 89 mL of 0.5 mol/L HCl aq. were added, the solution was stirred for 5 minutes. Following this, 444 mL of 0.5 mol/L HCl aq. were added dropwise and then the solution was cooled with water to make inner temperature 25° C. The precipitated crystals were filtered and, after washing with 733 mL of purified water, they were dried for 8 hours at 65° C. by blower to obtain 72.6 g (yield 78%) of the new type crystals of compound (I) as white crystalline powder.

Melting point: 132-133° C. (hot plate method). Mass analysis: EI-MS(m/z): 235, 451($M^+$, base peak). Angle of rotation: $[\alpha]_D^{25}$ +29° (C=1.0, MeCN). Elemental analysis: Anal. Calcd. for $C_{26}H_{26}FNO_5$(MW 451.49): C, 69.17; H, 5.80; N, 3.10. Found: C, 69.03; H, 5.84; N, 3.11. NMR spectra: $^1$H-NMR(DMSO-$d_6$, ppm, 400 MHz)δ: 0.85(3H, t, J=7.8 Hz), 1.41~1.53(2H, m), 2.38~2.45(1H, m), 2.65(1H, dd, J=6.4, 13.7 Hz), 2.76(1H, dd, J=8.3, 13.7 Hz), 3.85(3H, s), 4.45(2H, d, J=6.4 Hz), 6.93~6.97(2H, m), 7.01~7.05(3H, m), 7.16~7.22(2H, m), 7.27(1H, dd, J=2.4, 8.8 Hz), 7.33(2H, d, J=8.3 Hz), 7.57(1H, d, J=2.4 Hz), 8.66(1H, t, J=6.4 Hz), 12.09(1H, s). Purity test: HPLC relative purity; 99.9% [HPLC conditions: measuring wavelength; 210 nm, column; Inertsil ODS-3 (4.6 mmID×250 mm), precolumn; Inertsil ODS-3 (4.0 mmID×10 mm), mobile phase; MeCN/diluted phosphoric acid (1→1000)=60:40, column temperature; 30° C., flow rate ; 1.0 mL/min, injection level(solvent); 4 μg/2 μL(MeCN)]. Optical purity test: HPLC relative purity; 100% ee [HPLC conditions: measuring wavelength; 210 nm, column; CHIRALPAK AD-RH (4.6 mmID×150 mm), precolumn; Inertsil ODS-3 (4.0 mmID×10 mm), mobile phase; diluted phosphoric acid (1→1000): acetonitrile (MeCN)=55:45, column temperature ; 40° C., flow rate; 1.0 mL/min, injection level(solvent); 4 μg/2 μL(MeCN)].

EXAMPLE 2

Preparation of new type crystals of (S)-2-[[3-[N-[4-[(4-fluorophenoxy)phenyl]methyl]carbamoyl]-4-methoxyphenyl]methyl]butanoic acid (compound (I))

To a solution of 50.2 g (100 mmol) of benzyl 5-[3-[4-(R)-benzyl-2-oxo-1,3-oxazolidine-3-yl]-2-(S)-ethyl-3-oxo-propyl]-2-methoxybenzoate (Jpn. Kokai Tokkyo Koho JP 2001-55367, Example 165)in 351 mL of ethyl acetate (AcOEt) were added 3.34 g of 10% palladium on carbon (Pd—C) (dry article), and the mixture was stirred for 2 hours at 35° C. under an atmosphere of hydrogen. After the catalyst was filtered off, the reaction mixture was concentrated under reduced pressure to obtain colorless oily product (41.2 g). Triethylamine (30.4 g, 300 mmol) was added to a solution of the oily product (41.2 g) obtained in 200 mL of dehydrated N,N-dimethylformamide and, after ethyl chloroformate (10.0 mL, 105 mmol) was added at inner temperature of 5° C. under cooling with ice water, the mixture was stirred for 1 hour. [4-(4-Fluorophenoxy)phenyl]methylamine hydrochloride (26.6 g, 105 mmol) was put in the mixture, which was stirred for 1 hour. To the reaction mixture were added 400 mL of water, and the mixture was extracted with ethyl acetate (200 mL×twice). The ethyl acetate layer was washed with 1 mol/L aqueous solution of sodium hydroxide (100 mL), water (200 mL) and saturated brine (100 mL) in sequence, then dried over anhydrous sodium sulfate and concentrated under reduced pressure to obtain yellow oily product (61.1 g).

After 31% aqueous hydrogen peroxide (43.9 mL, 400 mmol) was added to a solution of the oily product (61.1 g) obtained in 488 mL of mixed solution of tetrahydrofuran-water (4:1) at inner temperature of 8° C. under cooling with ice water, a solution of lithium hydroxide monohydrate (6.71 g, 160 mmol) in 268 mL of water was added dropwise over 20 minutes at inner temperature of 8° C., and thereafter the mixture was stirred for 2 hours. A solution of sodium hydrogensulfite (41.6 g) in water (208 mL) was added dropwise to the reaction mixture and the mixture was stirred for 1 hour, which was then allowed to stand statically. After the organic layer was separated and concentrated under reduced pressure, the residue was dissolved into ethyl acetate (500 mL), which was extracted with 0.5 mol/L aqueous solution of sodium hydroxide (550 mL×twice). The aqueous layers were combined and, after 6 mol/L hydrochloric acid (125 mL) was added (pH value 1.91), the solution was extracted with ethyl acetate (400 mL, 150 mL). The ethyl acetate layers were combined, washed with saturated aqueous solution of sodium hydrogencarbonate (127 mL, pH value of washed liquid 6.95) and saturated brine (200 mL) in sequence, then dried over anhydrous sodium sulfate and concentrated under reduced pressure. Ethyl acetate (50 mL) and IPA (5 mL) were added to the solids (50.2 g) obtained and, after dissolved by refluxing, hexane (76 mL) was added and the inner temperature was made to be 65° C. The solution was stirred at room temperature under cooling by allowing to stand (crystal precipitation started at inner temperature of 59° C.). Thereafter, the solution was cooled with ice water at inner temperature of 30° C. and stirred for 1 hour at inner temperature of below 10° C. The precipitated crystals were collected by filtration (inner temperature 6° C.) and, after washing with a mixed solution (126 mL) of hexane/ethyl acetate (3:1), the crystals were dried for 5 hours at 50° C. by blower to obtain 35.0 g of crude crystals of compound (I). Ethanol (228 mL) was added to 35.0 g of crude crystals obtained and, after dissolved by heating (inner temperature 50° C.), the solution was filtered and purified water (121 mL) was added, followed by stirring under cooling with water (crystal precipitation started at inner temperature of 38° C.). After crystal precipitation, the suspension was stirred for 1 hour, cooled with ice water at inner temperature of 25° C., and stirred for 1 hour at inner temperature of below 10° C. The precipitated crystals were collected by filtration (inner temperature 6° C.) and, after washing with 25% ethanol/water (126 mL), the crystals were dried for 13.5 hours at 50° C. by blower to obtain 34.7 g (77%) of the new type crystals of compound (I) as white needle-like crystals.

Mp 131° C. (hot plate method). $[\alpha]_D^{24}=+30°$ (c=1.0, acetonitrile). Anal. Calcd. for $C_{26}H_{26}FNO_5$(MW 451.49): C, 69.17; H, 5.80; N, 3.10. Found: C, 69.19; H, 5.64; N, 3.34. EI-MS m/z: 235, 451[M$^+$]. $^1$H-NMR(DMSO-$d_6$, 400 MHz) δ: 0.86(3H, t, J=7.3 Hz), 1.42-1.54(2H, m), 2.39-2.46(1H, m), 2.65(1H, dd, J=5.9, 13.7 Hz), 2.76(1H, dd, J=8.3, 13.7 Hz), 3.85(3H, s), 4.45(2H, d, J=6.4 Hz), 6.95(2H, d, J=8.8 Hz), 7.00-7.05(3H, m), 7.17-7.23(2H, m), 7.27(1H, dd, J=2.4, 8.3 Hz), 7.33(2H, d, J=8.3 Hz), 7.58(1H, d, J=2.0 Hz), 8.66(1H, t, J=5.9 Hz), 12.08(1H, s).

EXAMPLE 3

Conversion of Crystal Form

Into 9.9 mL of ethanol were dissolved by heating (45° C.) 1.53 g of the old type crystals (melting point 95~96° C.) of compound (I) obtained through the conventional process (Example 174 of Jpn. Kokai Tokkyo Koho JP 2001-55367). To this were added 5.4 mL of water, the solution was cooled by allowing to stand, and then cooled (5° C.) with ice water. The precipitated crystals were filtered and washed with 7.5 mL of 25% ethanol/water. These were dried for 2 hours at 50° C. under reduced pressure to obtain 1.48 g (96.7%) of the new type crystals of compound (I).

Melting point: 132~133° C. (hot plate method)

TESTING EXAMPLE 1

Measurement of X-Ray Powder Diffraction

The X-ray powder diffraction was measured by CuKα line, employing wide-angle goniometer of X-ray diffraction apparatus RINT2200 from Rigaku Co. The diffraction angle (2θ) and the relative intensity (cps) for the crystals of the compound in said examples are shown in FIG. 1. The X-ray powder diffraction pattern for the crystals (old type crystals) obtained through the conventional process is shown in FIG. 2. As a result, the crystals obtained in the examples of the invention exhibit a characteristic diffraction pattern at at least 2θ=17.7°, 19.0° and 24.1°, which differs from that of the conventional crystals.

TESTING EXAMPLE 2

Differential Thermal Analysis (DTA) and Thermogravimetry (TG)

The thermal stability of crystals was compared by using apparatus for thermal analysis (SII: TG/DTA6200). FIG. 3 shows a chart of thermal analysis and thermogravimetry of the new type crystals of compound (I) and FIG. 4 those of the old type crystals. With the new type crystals, the endothermic phenomenon due to transition was seen from 131.4° C. and the endothermic peak due to melting was shown at 132.0° C. On the other hand, the old type crystals showed the endothermic peak at 109.7° C. Moreover, in all cases, no weight change was recognized. From this fact, it has become clear that the new type crystals are thermally stable crystals.

Utilizability in the Industry

It is possible to obtain stable and homogeneous new type crystals with no residual organic solvent by recrystallizing the crystals of compound (I) obtainable through the conventional process from a lower alcoholic suitable solvent, thus obtaining new type crystals, and further by performing acid-base treatment. The homogeneous and stable new type crystals to be provided according to the invention have no hygroscopicity and make a stable supply possible in terms of preparation, which is very advantageous in the industrial production of compound (I).

Figure 1:
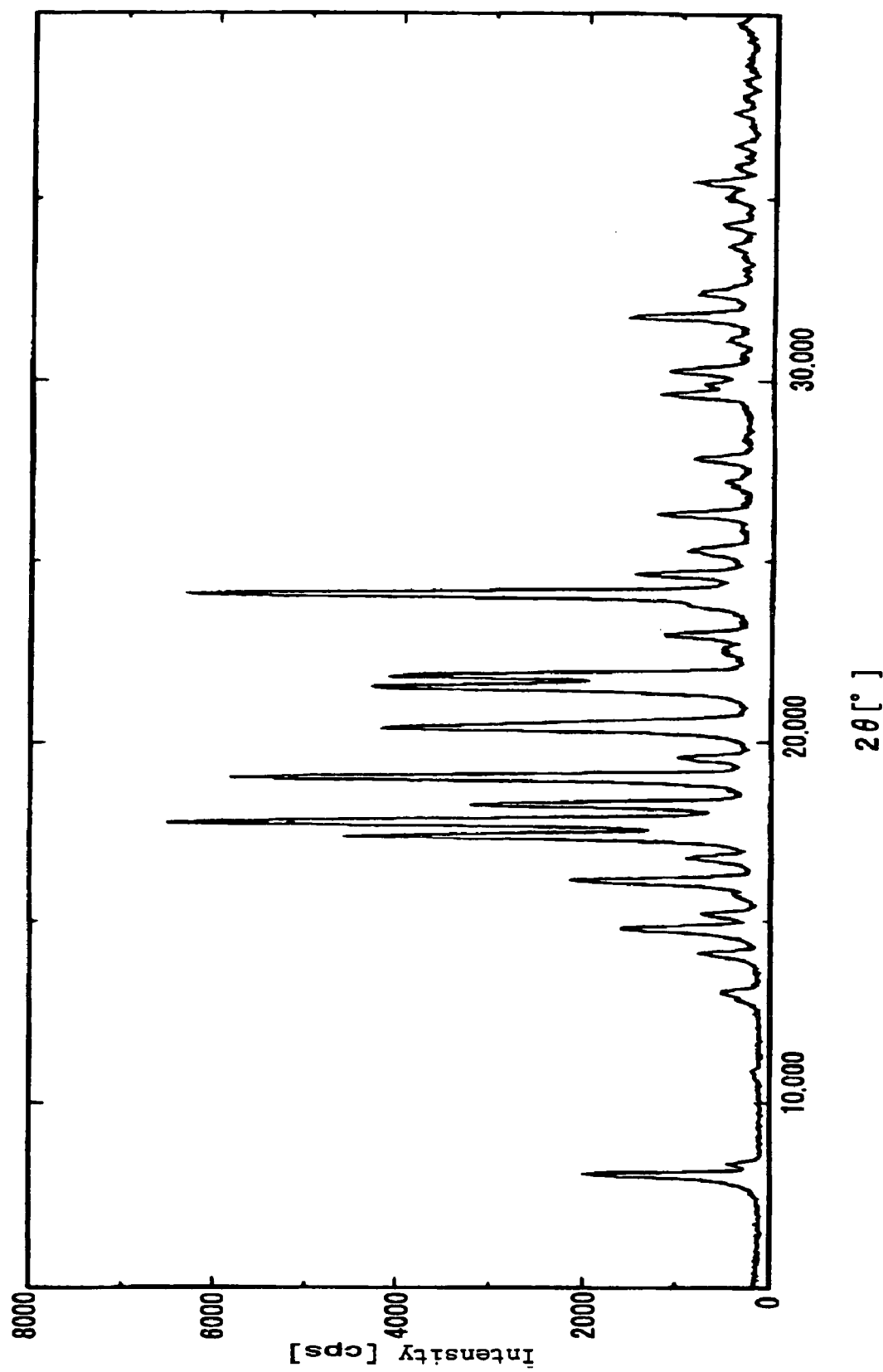
FIG. 1 The X-ray powder diffraction diagram of the inventive new type crystals.
Figure 2:
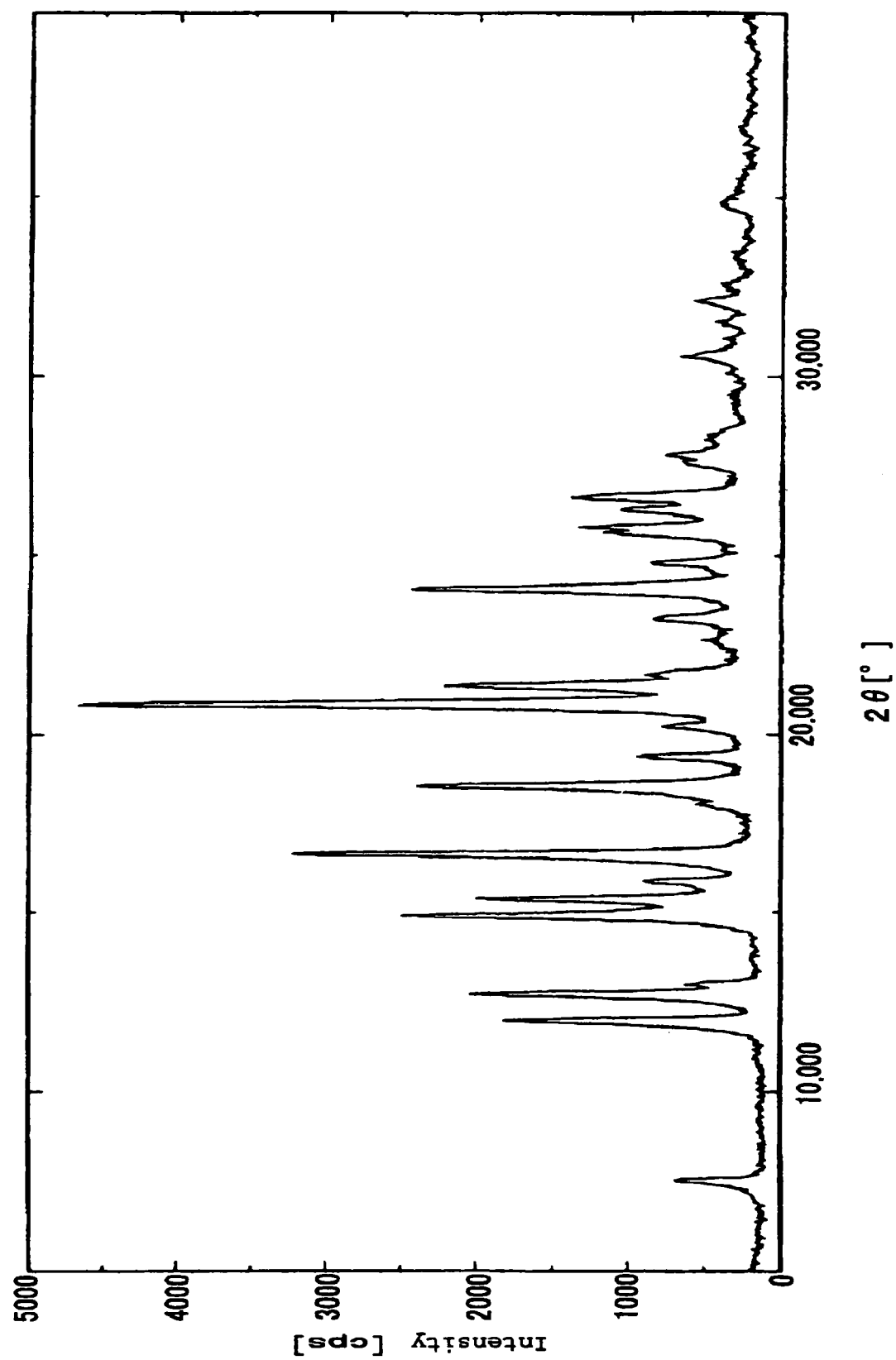
FIG. 2 The X-ray powder diffraction diagram of the old type crystals.
Figure 3:
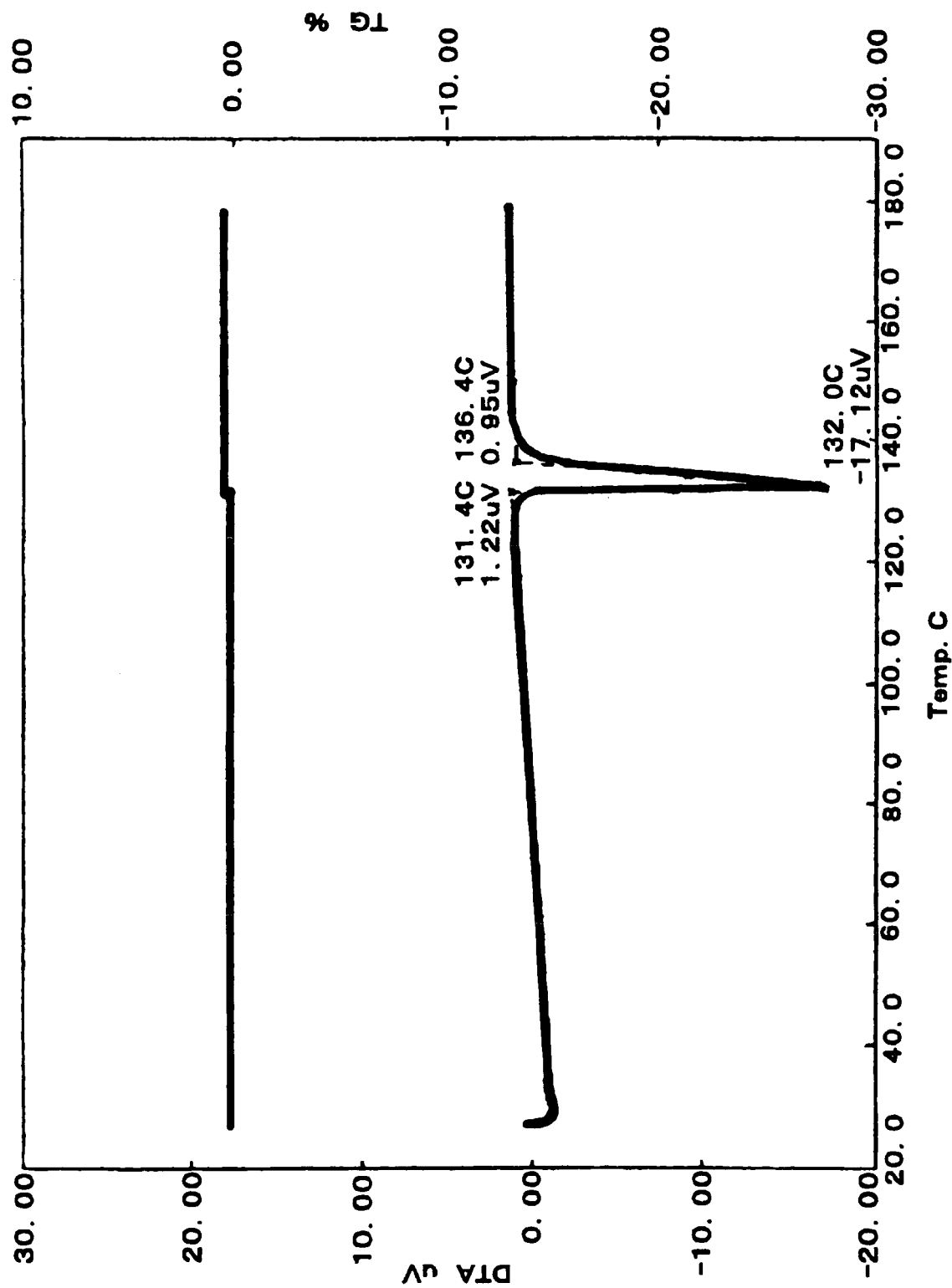
FIG. 3 The thermometry diagram of the inventive new type crystals.
Figure 4:
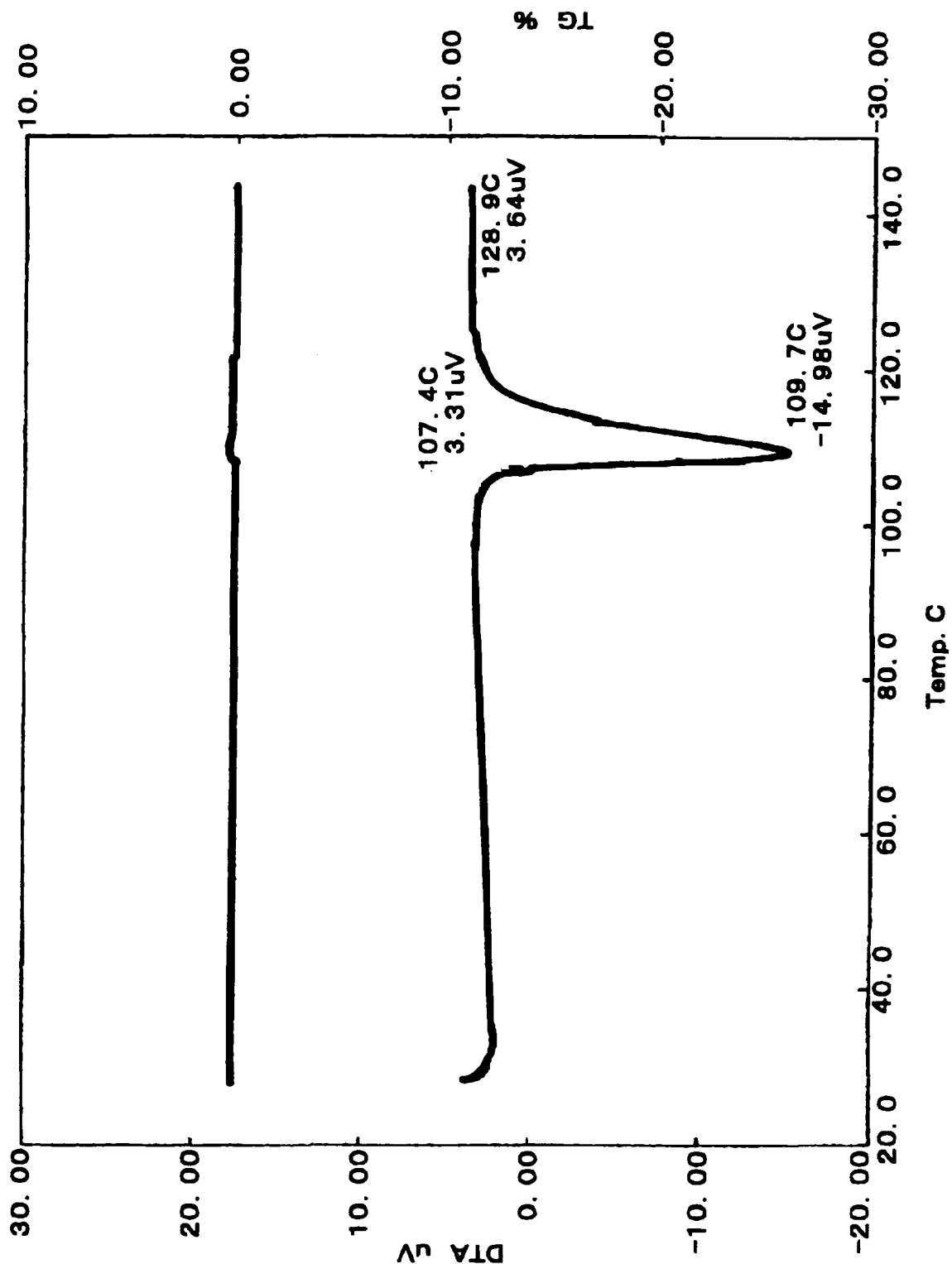
FIG. 4 The thermometry diagram of the old type crystals.

The invention claimed is:

1. New type crystals of (S)-2-[[3-[N-[4-[(4-fluorophenoxy) phenyl]methyl]carbamoyl]-4-methoxyphenyl]methyl]butanoic acid (compound (I)), characterized by exhibiting the diffraction angles (2θ) at at least 17.7°, 19.0° and 24.1° in the X-ray powder diffraction.

2. A process for preparing the new type crystals of claim 1, characterized by recrystallizing the compound (I) from a suitable solvent.

3. A process for preparing the new type crystals of claim 1, characterized by recrystallizing the compound (I) from a lower alcohol or water-containing lower alcohol and then performing acid-base treatment.

4. A medicinal drug containing the crystals of claim 1.

* * * * *